(12) United States Patent
Manlove

(10) Patent No.: US 8,452,570 B2
(45) Date of Patent: May 28, 2013

(54) SYSTEMS AND APPARATUSES FOR TESTING BLOOD GLUCOSE MEASUREMENT ENGINES

(75) Inventor: Nathan Manlove, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 753 days.

(21) Appl. No.: 12/641,594

(22) Filed: Dec. 18, 2009

(65) Prior Publication Data

US 2011/0152655 A1 Jun. 23, 2011

(51) Int. Cl.
*G06F 19/00* (2011.01)
*A61B 5/145* (2006.01)

(52) U.S. Cl.
USPC .......................................... 702/183; 600/365

(58) Field of Classification Search
CPC ....................................................... G06F 19/00
USPC .................. 702/183; 600/300, 309, 310, 365
See application file for complete search history.

(56) References Cited

U.S. PATENT DOCUMENTS

| | | | |
|---|---|---|---|
| 5,124,661 A | 6/1992 | Zelin et al. | |
| 5,594,906 A | 1/1997 | Holmes, II et al. | |
| 6,641,533 B2 * | 11/2003 | Causey et al. | 600/300 |
| 7,914,449 B2 * | 3/2011 | Kouchi et al. | 600/365 |
| 2006/0248398 A1 * | 11/2006 | Neel et al. | 714/33 |
| 2007/0002791 A1 | 1/2007 | Kasprzyk et al. | |
| 2007/0088521 A1 | 4/2007 | Shmueli et al. | |

FOREIGN PATENT DOCUMENTS

| | | |
|---|---|---|
| DE | 36 02 171 A1 | 9/1987 |
| WO | 2010/138817 A1 | 12/2010 |

\* cited by examiner

*Primary Examiner* — Bryan Bui
(74) *Attorney, Agent, or Firm* — Dinsmore & Shohl LLP

(57) ABSTRACT

A system for testing a blood glucose measurement engine includes a host device emulator having a measurement engine port communicatively coupled to a communications port and electrically coupled to a power supply. A diagnostic computer may be communicatively coupled to the communications port of the host device emulator. The diagnostic computer may include a processor and a memory having computer readable and executable instructions. When the blood glucose measurement engine is communicatively coupled to the measurement engine port, the host device emulator simulates connection to a host device by facilitating the communication of signals between the diagnostic computer and the blood glucose measurement engine. The processor executes the computer readable and executable instructions to: transmit control signals and diagnostic signals to the measurement engine, receive and analyze data signals transmitted from the measurement engine, and monitor a glucose measurement process performed by the measurement engine.

19 Claims, 13 Drawing Sheets

SYSTEMS AND APPARATUSES FOR TESTING BLOOD GLUCOSE MEASUREMENT ENGINES

TECHNICAL FIELD

The present specification generally relates to measurement engines for determining blood glucose levels and, more specifically, to systems and apparatuses for use in testing blood glucose measurement engines.

BACKGROUND

Portable handheld medical diagnostic devices are often employed to measure concentrations of biologically significant components in bodily fluids, such as, for example, glucose concentration in blood. The portable handheld medical diagnostic devices and their accessories may work together to measure the amount of glucose in blood and may be used by persons having diabetes or healthcare professionals to monitor blood glucose in the home, in a healthcare facility or at other locations.

For people with diabetes, regular testing of blood glucose levels can be an important part of diabetes management. Thus, it is desirable to provide medical diagnostic devices, such as blood glucose measurement devices, that are portable and easy to use. To that end, various blood glucose measurement devices have been introduced which are portable. Other, modular blood glucose measurement devices have been introduced which may be integrated in a host device, such as a personal medication pump (e.g., an insulin pump) or personal consumer electronics devices (e.g., cell phones, smart phones, personal digital assistants, portable media players, etc.). However, ensuring the compatibility and functionality of the modular blood glucose measurement devices with such host devices presents unique challenges as such devices are continuously modified, upgraded and otherwise improved upon.

Accordingly, a need exists for alternative apparatuses and methods for testing blood glucose measurement engines used with host devices.

SUMMARY

In one embodiment, a system for testing a blood glucose measurement engine includes a host device emulator having a measurement engine port communicatively coupled to a communications port and electrically coupled to a power supply. A diagnostic computer may be communicatively coupled to the communications port of the host device emulator. The diagnostic computer may include a processor and a memory having computer readable and executable instructions. When the blood glucose measurement engine is communicatively coupled to the measurement engine port, the host device emulator simulates connection to a host device by facilitating communication of data signals, control signals and diagnostic signals between the diagnostic computer and the blood glucose measurement engine. The computer readable and executable instructions may be executed by the processor to: transmit control signals and diagnostic signals to the blood glucose measurement engine, receive and analyze data signals transmitted from the blood glucose measurement engine, and monitor a glucose measurement process performed by the blood glucose measurement engine.

In another embodiment, a host device emulator for facilitating communications between a blood glucose measurement engine and a diagnostic computer includes a power supply and a communication port electrically coupled to the power supply and communicatively connectable to the diagnostic computer. The host device emulator also includes a measurement engine port communicatively coupled to the communications port and electrically coupled to at least one indicator and the power supply. The measurement engine port is also communicatively connectable to the blood glucose measurement engine. A host device port may be electrically coupled to the power supply and communicatively coupled to the measurement engine port and the communications port. The host device port is also communicatively connectable to the host device and, wherein the measurement engine port, the host device port and the communications port are operable to: facilitate communication of data signals, control signals and diagnostic signals between the diagnostic computer and the blood glucose measurement engine, facilitate communication of data signals and control signals between the host device and the blood glucose measurement engine, and facilitate use of the diagnostic computer to monitor data signals and control signals between the host device and the blood glucose measurement engine.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
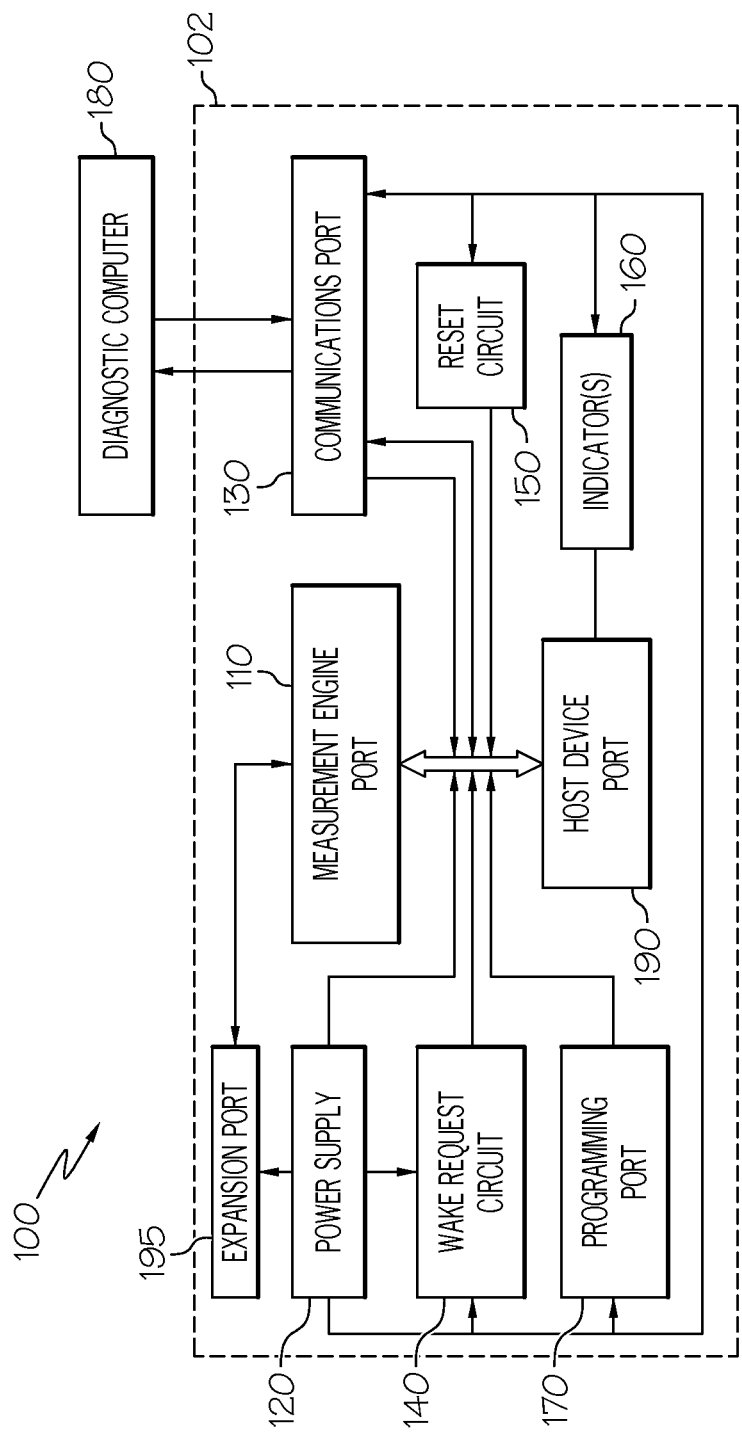
FIG. 1 schematically depicts a system for testing a blood glucose measurement engine utilizing a host device emulator according to one or more embodiments shown and described herein.

FIG. 1 generally depicts one embodiment of a system for testing a blood glucose measurement engine. The system may comprise a host device emulator communicatively coupled to a diagnostic computer. The host device emulator may generally comprise a power supply circuit, a measurement engine port, at least one indicator, and a communications port arranged and interconnected on a printed circuit board. Various embodiments of the host device emulator and systems and methods utilizing the host device emulator to test blood glucose measurement engines will be described in more detail herein.

The phrase "blood glucose measurement engine", as used herein, refers to a device which is operable to analyze a sample of biological material, such as blood, to assess the level of glucose contained in the biological material. In the embodiments described herein, the blood glucose measurement engine is a modular device which may be incorporated into or otherwise coupled to a separate host device.

The phrase "host device", as used herein, refers to a portable electronic device to which the blood glucose measurement engine may be operatively coupled. A host device may be a personal diabetes management device ("PDM device"), a personal medication pump (such as an insulin pump), or similar portable electronic device including, without limitation, a mobile telephone, a smart phone, a personal digital assistant, a portable media player or the like.

Referring to FIG. 1, an embodiment of a system 100 for testing a blood glucose measurement engine is schematically depicted. It should be understood that the solid arrows generally indicate the interconnectivity of the various components of the system, including the various electronic components positioned on the host device emulator 102. It should also be understood that the solid arrows are indicative of electrical signals, such as control signals, diagnostic signals, and/or data signals, propagated between various components of the system. For example, the solid arrows between the diagnostic computer 180 and the communications port 130 may be indicative of data signals, diagnostic signals and/or control signals propagated between the diagnostic computer 180 and the communications port 130 of the host device emulator 102. Further, in the embodiments described herein, the solid arrows are indicative of a wired connection between various components. However, it should be understood that, in other embodiments, the solid arrows may be indicative of wireless connections between the various components of the system. For example, the diagnostic computer 180 and the host device emulator 102 may be wirelessly interconnected utilizing RF transceivers or similar wireless communication devices.

Referring to FIG. 1, one embodiment of a system for testing a blood glucose measurement engine is depicted in a functional block diagram. The system 100 includes a host device emulator 102 communicatively coupled to a diagnostic computer 180. The host device emulator simulates the connection between a blood glucose measurement engine and a host device. The host device emulator 102 may generally comprise a communications port 130 to which the diagnostic computer 180 is communicatively coupled. The communications port 130 may, in turn, be communicatively coupled to a measurement engine port 110 and a host device port. The measurement engine port 110 may be communicatively coupled to a blood glucose measurement engine (not shown) such that data signals, control signals and diagnostic signals may be propagated between the blood glucose measurement engine and the diagnostic computer 180 communicatively coupled to the communications port. Similarly, the host device port 190 may be communicatively coupled to a host device such that control signals and data signals may be propagated between the host device and a blood glucose measurement engine communicatively coupled to the measurement engine port 110.

The diagnostic computer 180 comprises a processor (not shown) and a memory (not shown). In one embodiment, the memory is operable to store computer readable and executable instructions for operating, testing, programming and/or reprogramming a blood glucose measurement engine communicatively coupled to the measurement engine port 110 of the host device emulator 102. The processor is operable to execute the computer readable and executable instructions stored in the memory of the diagnostic computer 180. In this embodiment, the diagnostic computer functions as a simulated host device to which the blood glucose measurement engine is operatively coupled or otherwise integrated. For example, the diagnostic computer may simulate the functionality of a host device, such as a personal medication pump or similar portable electronic device, which would otherwise control and/or supervise the blood glucose measurement engine in a master/slave relationship with the blood glucose measurement engine such that blood glucose tests performed by the blood glucose measurement engine are initiated by the host device and the results of the blood glucose measurements performed by the blood glucose measurement engine are received and utilized by the host device. Accordingly, it should be understood that the diagnostic computer, specifically the processor of the diagnostic computer, is operable to provide control signals and diagnostic signals to the blood glucose measurement engine via the communications port of the host device emulator 102 thereby initiating blood glucose measurements by the blood glucose measurement engine and generally controlling the operation of the blood glucose measurement engine.

For example, the computer readable and executable instructions stored in the memory of the diagnostic computer 180 may be performed by the processor to initiate a blood glucose measurement with the blood glucose measurement engine by sending a control signal to the blood glucose measurement engine via the host device emulator 102. Alternatively, one or more diagnostic signals may be transmitted to the blood glucose measurement engine via the host device emulator. The diagnostic signals may be operable to step the blood glucose measurement engine through each programmed instruction of the measurement process and pause the blood glucose measurement engine after each instruction has been performed.

The diagnostic computer 180 is operable to receive data from the blood glucose measurement engine via the communications port 130 of the host device emulator 102 and store the data in memory for analysis. The memory operatively associated with the diagnostic computer 180 may also contain computer readable and executable instructions for analyzing the data received from the blood glucose measurement engine to assess the operability and functionality of the blood glucose measurement engine and diagnose any errors in the operation of the blood glucose measurement engine, which instructions may be executed by the processor. In the case where the analyzed data is derived from a blood glucose measurement performed on a glucose standard, such as a solution having a known glucose concentration, the memory of the diagnostic computer 180 may also contain computer readable and executable instructions which may be performed by the processor to calibrate the blood glucose measurement engine based on the data derived from the measurement performed on the glucose standard.

In another embodiment, the memory of the diagnostic computer 180 may also contain computer readable and executable instructions for monitoring signals transmitted between a host device coupled to the host device port 190 of the host device emulator 102 and a blood glucose measurement engine coupled to the measurement engine port 110 of the host device emulator 102, which instructions may be executed by the processor of the diagnostic computer 180. For example, the control signals and data signals transmitted between the host device and the blood glucose measurement engine are also transmitted to the diagnostic computer 180 via the communications port 130 of the host device emulator 102. The diagnostic computer 180 is operable to record the control signals and data signals in memory and/or display the signals in real time. The memory of the diagnostic computer may also comprise computer readable and executable instructions for analyzing the control signals and data signals transmitted between the blood glucose measurement engine and the host device.

Referring now to FIGS. 1-10, FIGS. 2-10 schematically depict embodiments of the various electronic components and circuitry which make up the functional blocks of the system of FIG. 1 and, more specifically, the various electronic components from which the host device emulator 102 is constructed. FIGS. 2-10 also depict the circuit level interconnectivity between the various functional blocks depicted in FIG. 1. The host device emulator 102 will now be described in more detail with specific reference to FIGS. 1-10.

As described above, the host device emulator 102 simulates the connection between a blood glucose measurement engine and a host device in which the blood glucose measurement engine may be integrated or otherwise coupled. In the embodiment shown in FIG. 1 the host device emulator 102 comprises a measurement engine port 110 to which a blood glucose measurement engine (not shown) may be communicatively coupled. The measurement engine port 110 generally comprises a printed circuit board (PCB) connector to which a blood glucose measurement engine may be communicatively coupled, as will be described in more detail herein. However, it should be understood that other, similar connectors may be used, including, without limitation, wired or wireless connections. In the embodiment of the measurement engine port 110 depicted in FIG. 2, the measurement engine port 110 comprises a printed circuit board connector 112 such as a DF17 (2.0)-30DP-0.5V(57) surface mount connector manufactured by Hirose Electric Company. The connector 112 is operable to receive a printed circuit board of a blood glucose measurement engine such that the blood glucose measurement engine is mechanically and communicatively coupled to the host device emulator 102. The connector 112 also facilitates communicatively coupling the blood glucose measurement engine to various other components of the host device emulator 102 as will be described in more detail herein.

Figure 2:
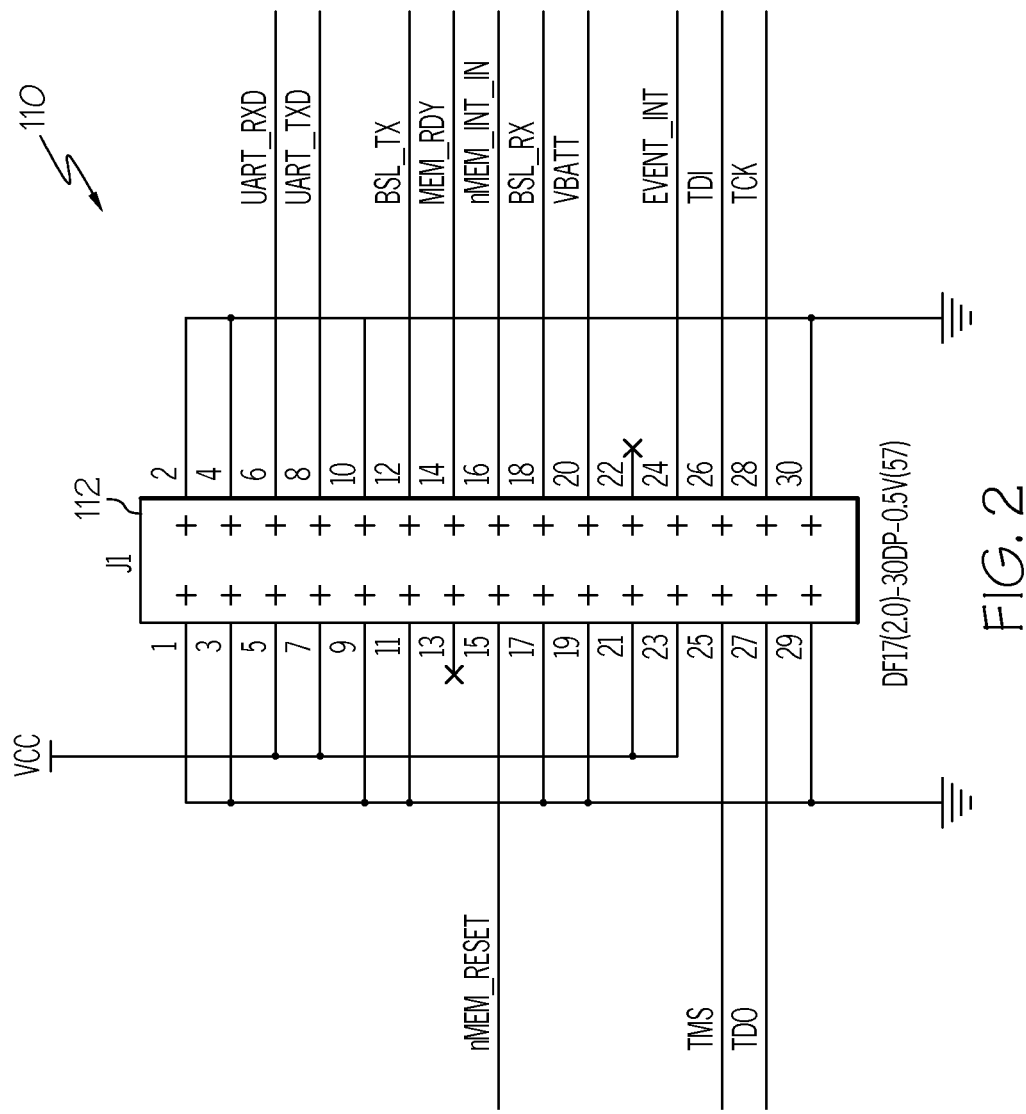
FIG. 2 schematically depicts a measurement engine port of a host device emulator according to one or more embodiments shown and described herein.
Figure 3:
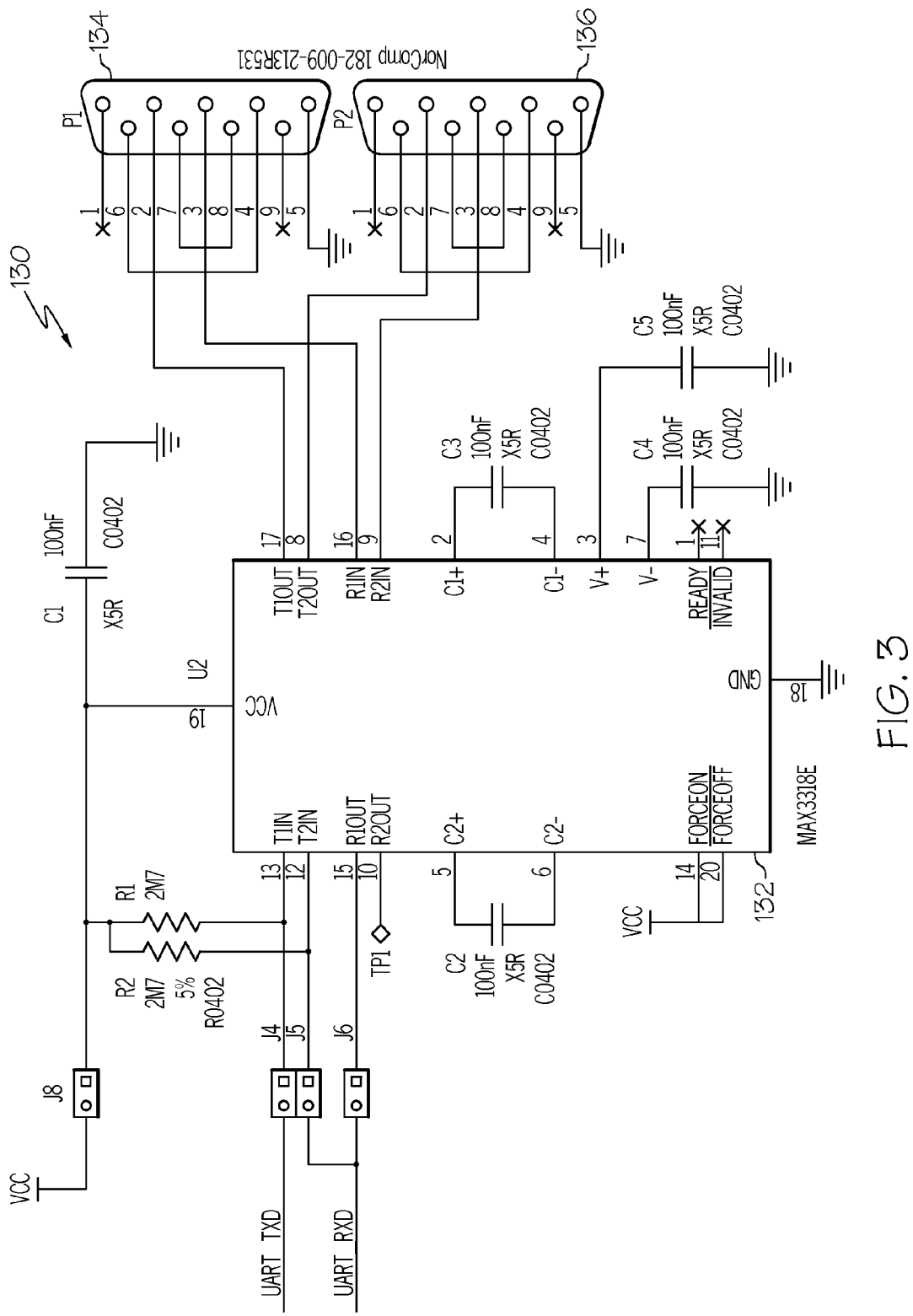
FIG. 3 schematically depicts a communications port of a host device emulator according to one or more embodiments shown and described herein.

As described above, the measurement engine port 110 is communicatively coupled to the communications port 130, which, in turn, may be communicatively coupled to the diagnostic computer 180. In the embodiment of the communications port 130 depicted in FIG. 3, the communications port 130 comprises a wired RS 232 interface 132 which is operable to convert electrical input signals received from the blood glucose measurement engine to standardized serial communication signals which may be processed by the diagnostic computer 180. For example, the RS 232 interface 132 may include a MAX 3318E RS 232 Compatible Transceiver manufactured by Maxim Integrated Products, as depicted in FIG. 3. The RS 232 transceiver is communicatively coupled to the printed circuit board connector 112 of the measurement engine port 110 as indicated in FIGS. 2 and 3. In the embodiment of the RS 232 interface 132 shown in FIG. 3, a pair of DB9 female connectors 134, 136, such as NORCOMP 182-009-213R531 9 pin connectors manufactured by Norcomp, Inc., are connected to the RS 232 interface to facilitate coupling the RS 232 interface to the diagnostic computer 180.

While FIG. 3 depicts a wired RS 232 interface 132, it should be understood that, in other embodiments, the interface may be wireless. For example, RF transceivers, IR transceivers or similar wireless communications devices may be used to communicatively couple the measurement engine port 110 to the diagnostic computer 180.

Still referring to FIGS. 1-10, the host device port 190 is communicatively coupled to the measurement engine port 110 such that control and/or data signals may be exchanged between a host device (not shown) communicatively coupled to the host device port 190 and a blood glucose measurement engine communicatively coupled to the measurement engine port 110. The host device port 190 generally comprises a printed circuit board (PCB) connector to which a host device may be communicatively coupled. For example, in the embodiment of the host device port 190 depicted in FIG. 9, the host device port 190 comprises a printed circuit board connector 192 such as a DF17(4.0)-30DS-0.5V(57) surface mount connector manufactured by Hirose Electric Company. In this embodiment, a printed circuit board of the host device may be removably inserted in the printed circuit board connector 192 such that the host device is mechanically and communicatively coupled to the host device emulator 102. However, it should be understood that other, similar connectors may be used, including, without limitation, wired or wireless connectors.

Figure 9:
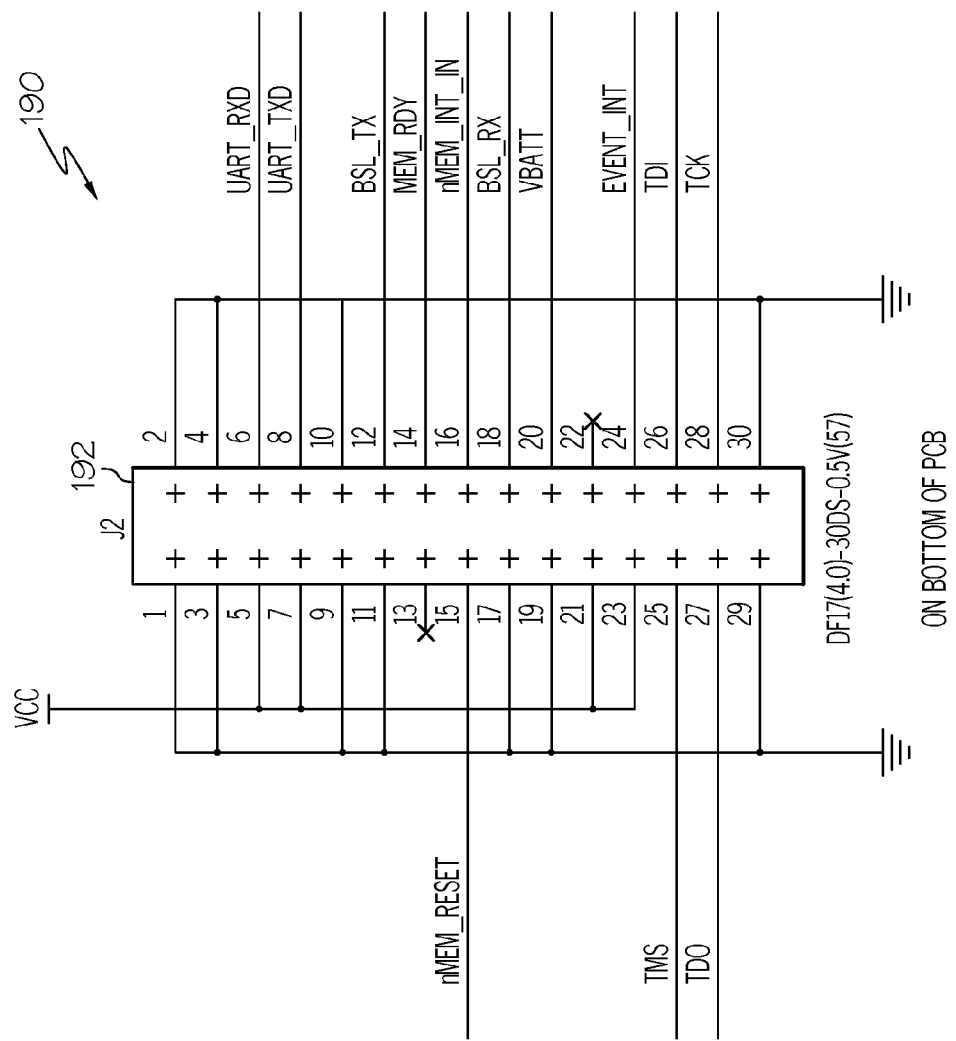
FIG. 9 schematically depicts a host device port of a host device emulator according to one or more embodiments shown and described herein.

In the embodiments described herein, the host device port 190 is also communicatively coupled to the communications port 130 as depicted in FIGS. 1, 3 and 9. Accordingly, it should be understood that the communications port 130 and host device port 190 facilitate the exchange of electrical signals, such as control signals and/or data signals, between a host device communicatively coupled to the host device port 190 and a diagnostic computer 180 communicatively coupled to the communications port 130. Further, it should also be understood that the host device port 190, the measurement engine port 110, and the communications port 130 facilitate use of the diagnostic computer 180 coupled to the communications port 130 to monitor electronic signals exchanged between a host device communicatively coupled to the host device port 190 and a blood glucose measurement engine communicatively coupled to the measurement engine port 110.

At least one indicator 160 is electrically coupled to the measurement engine port 110. In one embodiment, the at least one indicator 160 provides a visual and/or audible signal indicative of signals propagated between the diagnostic computer 180 communicatively coupled to the communications port 130 and a blood glucose measurement engine communicatively coupled to the measurement engine port 110. In addition, the at least one indicator can provide a visual and/or audible indication of the status of the blood glucose measurement engine communicatively coupled to the measurement engine port 110. For example, the at least one indicator may provide an indication that the blood glucose measurement engine is "Ready" or that the blood glucose measurement engine is "Working" such as when the blood glucose measurement engine is processing a test sample, sending or receiving data, powering on (i.e., "waking") and/or receiving instructions from the diagnostic computer. The at least one indicator may also provide a visual indication that power is being supplied to the host device emulator 102.

Figure 8:
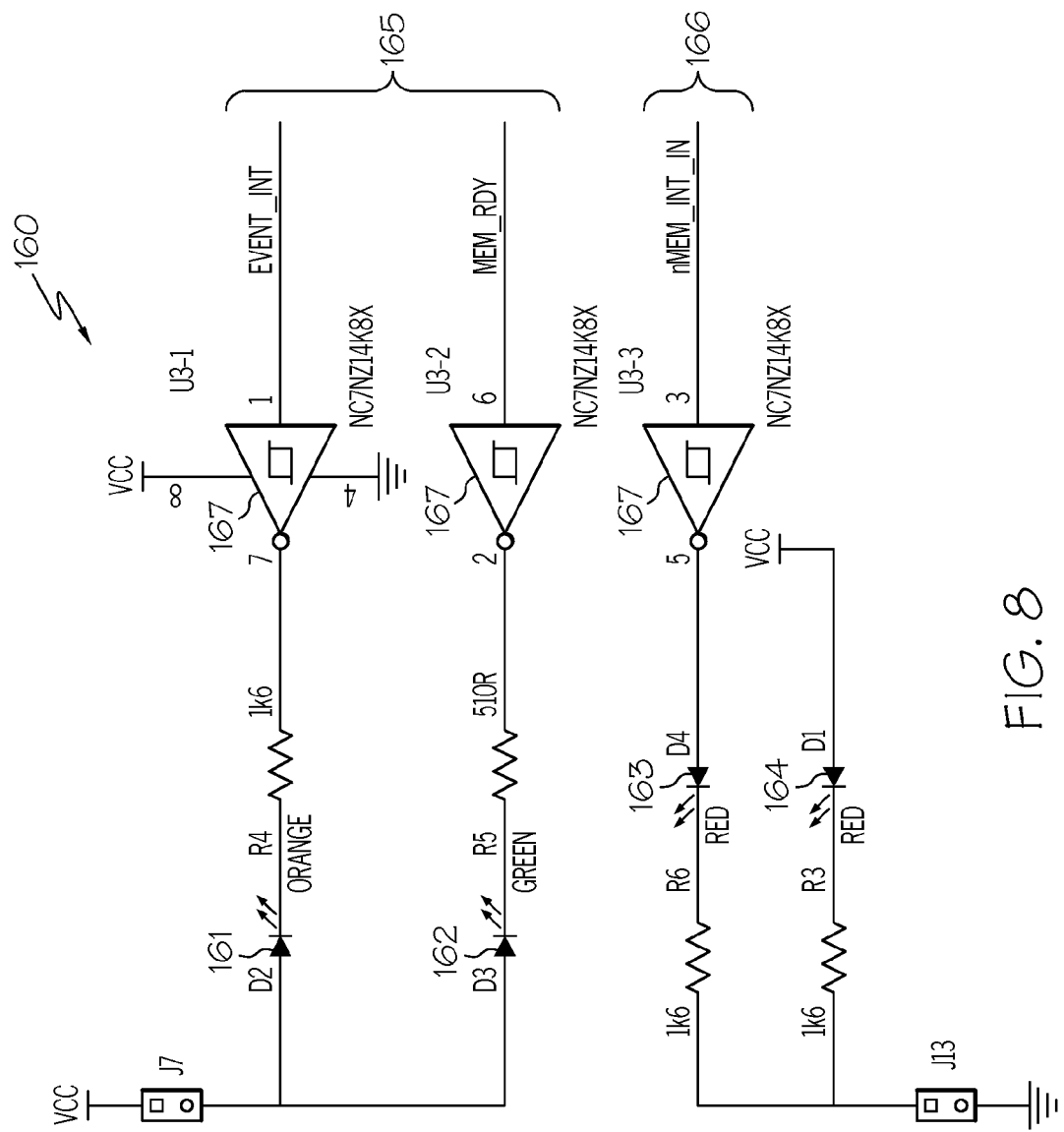
FIG. 8 schematically depicts indicator circuit(s) of a host device emulator according to one or more embodiments shown and described herein.

In the embodiments of the host device emulator described herein, the host device emulator comprises four visual indicators, specifically light emitting diodes (LEDs), contained in two indicator circuits 165, 166 shown in FIG. 8. The first indicator circuit 165 comprises an orange LED 161 and a green LED 162. Each LED 161, 162 is electrically coupled to a logic inverter 167, such as the NC7NZ14K8X Tinylogic UHS Inverter with Schmitt Trigger Input manufactured by Fairchild Semiconductor. The orange LED 161 is electrically coupled to the measurement engine port 110 and the host device port 190 as shown in FIGS. 2, 8 and 9 and is operable to provide a visual indication of electrical signals (i.e., measurement engine request signals) exchanged between a blood glucose measurement engine communicatively coupled to the measurement engine port 110 and a host device communicatively coupled to the host device port 190. For example, the orange LED 161 may flash and/or remain illuminated as electrical signals are exchanged and go dark when electrical signals are not being exchanged.

The green LED 162 is electrically coupled to the measurement engine port 110 and the host device port 190 as shown in FIGS. 2, 8 and 9 and is operable to provide a visual indication of the status of a blood glucose measurement engine communicatively coupled to the measurement engine port 110. For example, when the blood glucose measurement engine is "Ready", such as when the blood glucose measurement engine is ready to receive instructions from the host device and/or the diagnostic computer or transmit data to the host device and/or the diagnostic computer (i.e., a measurement engine ready signal), the green LED 162 is illuminated. However, when the blood glucose measurement engine is "Working", such as when the blood glucose measurement engine is performing a blood glucose test, sending or receiving data and/or receiving instructions from the host device or the diagnostic computer, the green LED 162 is dark.

The second indicator circuit 166 comprises two red LEDs 163, 164. The first red LED 163 is electrically coupled to a logic inverter 167, such as the NC7NZ14K8X Tinylogic UHS Inverter with Schmitt Trigger Input manufactured by Fairchild Semiconductor. The first red LED 163 is also electrically coupled to the measurement engine port 110 and the host device port 190 as shown in FIGS. 2, 8 and 9 and is operable to provide a visual indication of a wake request signal being transmitted from the wake request circuit 140 to a blood glucose measurement engine communicatively coupled to the measurement engine port 110. The second red LED 164 is electrically coupled to the power supply 120 (discussed further herein) and is illuminated when power is supplied to the host device emulator 102.

While the LEDs depicted in FIG. 8 have been referred to herein as being orange, green or red, it should be understood that the LEDs may be any suitable color so long as they provide a visual indication of the specified event.

Still referring to the embodiment of the host device emulator 102 depicted in FIGS. 1-10, the host device emulator 102 may also comprise a power supply 120. The power supply 120 may be electrically coupled to the measurement engine port 110, the communications port 130 and the at least one indicator 160 such that each component is supplied with power from the power supply 120. In the embodiments shown herein, the power supply 120 and measurement engine port 110 are configured such that, when a blood glucose measurement engine is communicatively coupled to the measurement engine port 110, the power supply 120 provides power to the blood glucose measurement engine through the measurement engine port 110 and, in doing so, the host device emulator 102 more closely emulates attachment of the blood glucose measurement engine to a host device.

Figure 4:
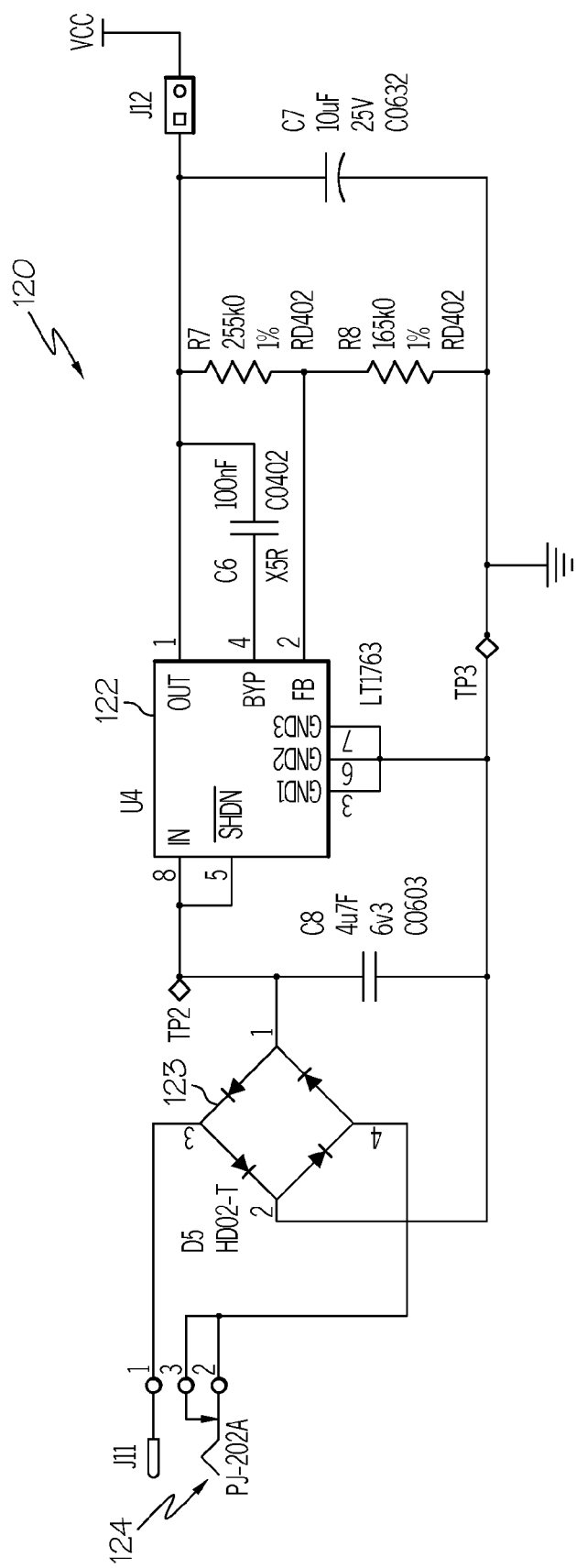
FIG. 4 schematically depicts a power supply circuit of a host device emulator according to one or more embodiments shown and described herein.

In the embodiment of the power supply 120 depicted in FIG. 4, the power supply comprises a power regulator 122, a rectification circuit 123 and a DC power jack 124, in addition to various electronic components (e.g., resistors and capacitors) which provide signal conditioning. For example, in the embodiment of the power supply 120 depicted in FIG. 4, the power regulator 122 is a LT 1763 500 mA, low noise, LDO micropower regulator manufactured by Linear Technology and electrical input is provided through a PJ-202A DC power jack manufactured by CUI, Inc. Using these components, the power supply 120 is operable to convert a 5 volt electrical input to a 3.1 VCC output signal which supplies power to the various components of the host device emulator 102.

Figure 7:
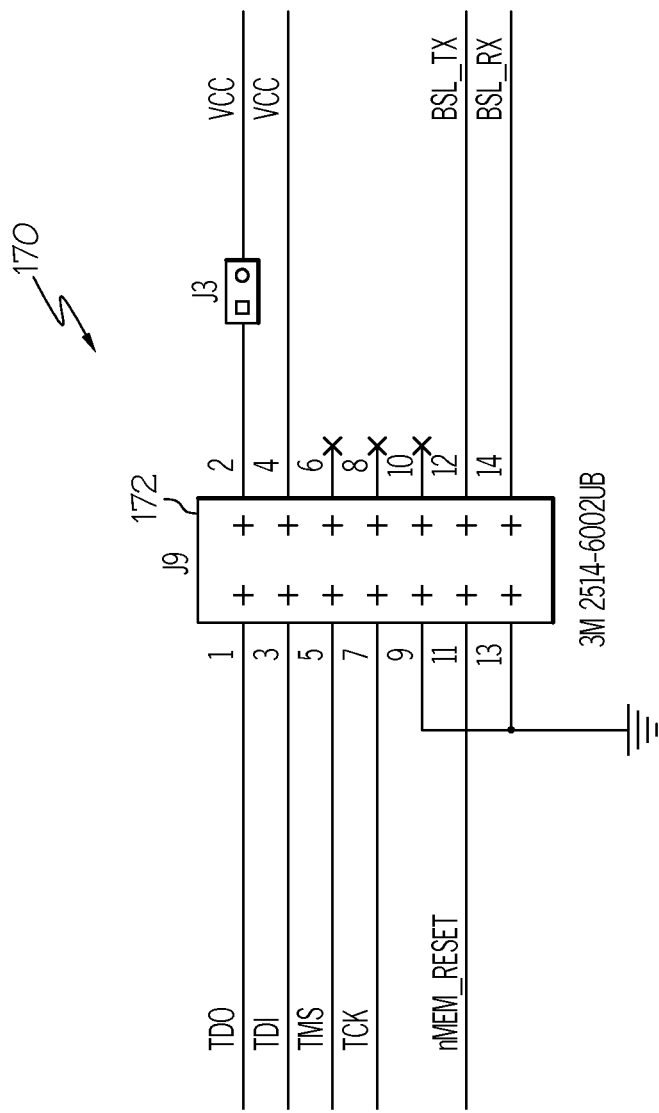
FIG. 7 schematically depicts a programming port of a host device emulator according to one or more embodiments shown and described herein.

In addition to the communications port 130, the measurement engine port 110, the power supply 120 and the at least one indicator 160, the host device emulator 102 may also include a programming port 170, a wake request circuit 140, an expansion port 195 and a reset circuit 150. For example, the programming port 170 may be communicatively coupled to the measurement engine port 110, the host device port 190, and the power supply 120 such that, when a blood glucose measurement engine is communicatively coupled to the measurement engine port 110, the programming port 170 may be communicatively coupled to the blood glucose measurement engine. The programming port 170 is also communicatively connectable to a computer (not shown) such that computer readable instructions may be downloaded from the computer through the programming port 170 and measurement engine port 110 and stored directly in a memory operatively associated with the blood glucose measurement engine. Use of a separate programming port facilitates the high speed transfer of computer readable instructions directly to the blood glucose measurement engine and thereby facilitates quickly programming or re-programming the blood glucose measurement engine. In the embodiment of the programming port 170 shown in FIG. 7, the programming port comprises a connector 172, such as a 2514-6002UB four walled header connector manufactured by 3M Interconnect Solutions Division. The connector 172 may be communicatively coupled to the measurement engine port 110 and the host device port 190 as depicted in FIGS. 2, 7 and 9.

In another embodiment (not shown), the programming port 170 may comprise a processor communicatively coupled to a memory in which computer readable and executable instructions are stored. The processor may be operable to upload the instructions to a blood glucose measurement engine communicatively coupled to the measurement engine port 110 thereby programming or reprogramming the blood glucose measurement engine.

Figure 5:
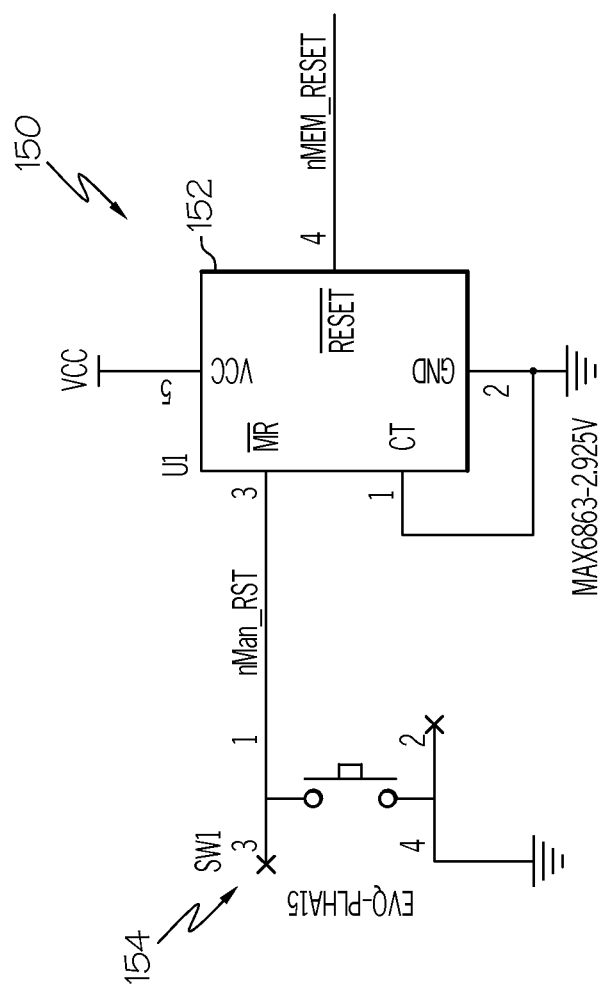
FIG. 5 schematically depicts a reset circuit of a host device emulator according to one or more embodiments shown and described herein.

The reset circuit 150 is communicatively coupled to the measurement engine port 110, the host device port 190 and the power supply 120 and facilitates providing a reset signal to the blood glucose measurement engine when the blood glucose measurement engine is communicatively coupled to the measurement engine port 110. The reset signal resets or restarts the blood glucose measurement engine communicatively coupled to the measurement engine port 110. In the embodiment of the reset circuit 150 depicted in FIG. 5, the reset circuit 150 comprises a manual reset switch 154 coupled to a supervisory reset circuit 152. For example, the switch may comprise an EVQ PLHA14 switch manufactured by Panasonic-ECG while the supervisory integrated circuit is a MAX6863 Nanopower Supervisory Circuit with Manual Reset manufactured by Maxim Integrated products. The manual reset switch 154 and supervisory reset circuit 152 are electronically coupled to the measurement engine port 110, the host device port 190 and the power supply 120 as shown in FIGS. 2, 5 and 9.

Figure 6:
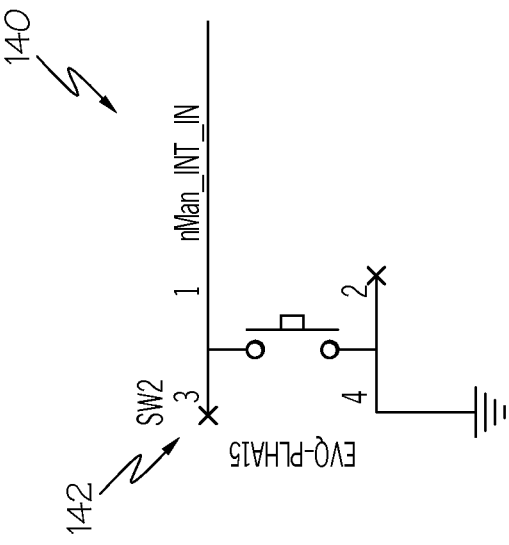
FIG. 6 schematically depicts a wake request circuit of a host device emulator according to one or more embodiments shown and described herein.

The wake request circuit 140 is communicatively coupled to the measurement engine port 110 and the power supply 120 and facilitates providing a wake request signal to the blood glucose measurement engine when the blood glucose measurement engine is mechanically and electrically coupled to the measurement engine port 110. The wake request signal causes the processor of the blood glucose measurement engine to power on from a "Standby" or "Sleep" mode such that the blood glucose measurement engine is ready to receive instructions from the diagnostic computer and/or the host device. The wake request circuit 140 comprises a manual switch for initiating the wake request signal to the blood glucose measurement engine. For example, the wake request switch 142 is electronically coupled to the measurement engine port 110 and the host device port 190 as shown in FIGS. 2, 6 and 9. The wake request switch 142 may comprise an EVQ PLHA14 switch manufactured by Panasonic-ECG.

Figure 10:
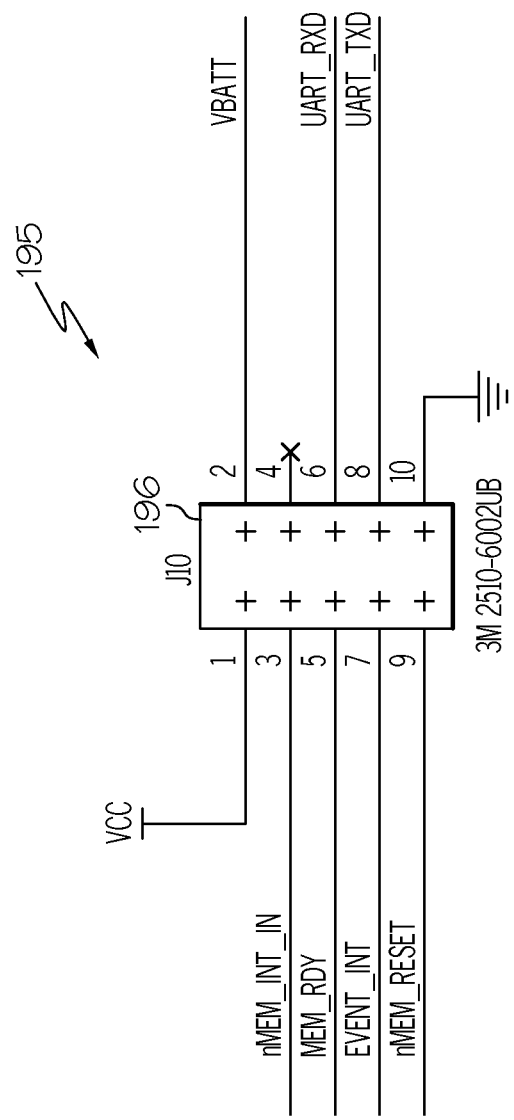
FIG. 10 schematically depicts an expansion port of a host device emulator according to one or more embodiments shown and described herein.

In the embodiment of the system 100 depicted in FIG. 1, the host device emulator 102 includes an expansion port 195. The expansion port 195 is communicatively coupled to the measurement engine port 110. Similar to the host device port 190, the expansion port 195 is communicatively connectable to a host device. Accordingly, it should be understood that the expansion port 195 facilitates the propagation of electronic signals, such as control signals and/or data signals, between a host device communicatively coupled to the expansion port 195 and a blood glucose measurement engine communicatively coupled to the measurement engine port 110. It should also be understood that the expansion port 195 facilitates coupling host devices having different interface structures and/or connectors to the host device emulator board and, as such, provides flexibility in testing blood glucose measurement engines designed for incorporation in different host devices. In the embodiment of the expansion port 195 shown in FIG. 10, the expansion port includes a connector, such as the 2510-6002UB four walled header connector manufactured by 3M Interconnect Solutions Division. The expansion port 195 may be communicatively and electrically coupled to the power supply 120, the measurement engine port 110 and the host device port 190 as depicted in FIGS. 2, 9 and 10.

In the embodiment of the host device emulator 102 depicted in FIG. 1, the host device emulator 102 includes a host device port 190 to which a host device may be communicatively coupled. However, it should be understood that, in other embodiments (not shown) the host device emulator 102 may be constructed without a host device port. In these embodiments the diagnostic computer 180 communicatively coupled to the communications port 130 is programmed to function as the host device and, in addition to any diagnostic or testing functions, the diagnostic computer also provides control signals and/or exchanges data with a blood glucose measurement engine communicatively coupled to the measurement engine port 110 thereby simulating the functionality of the host device.

While the host device emulator 102 depicted in FIG. 1 includes a wake request circuit 140, a programming port 170, a reset circuit 150 and an expansion port 195, it should be understood that other embodiments of the host device emulator may be constructed without one or more of these components. For example, it should be understood that the host device emulator may be constructed without the expansion port 195 or without the programming port 170. Alternatively or additionally, the host device emulator may be constructed without the wake request circuit or the reset circuit.

Figure 11:
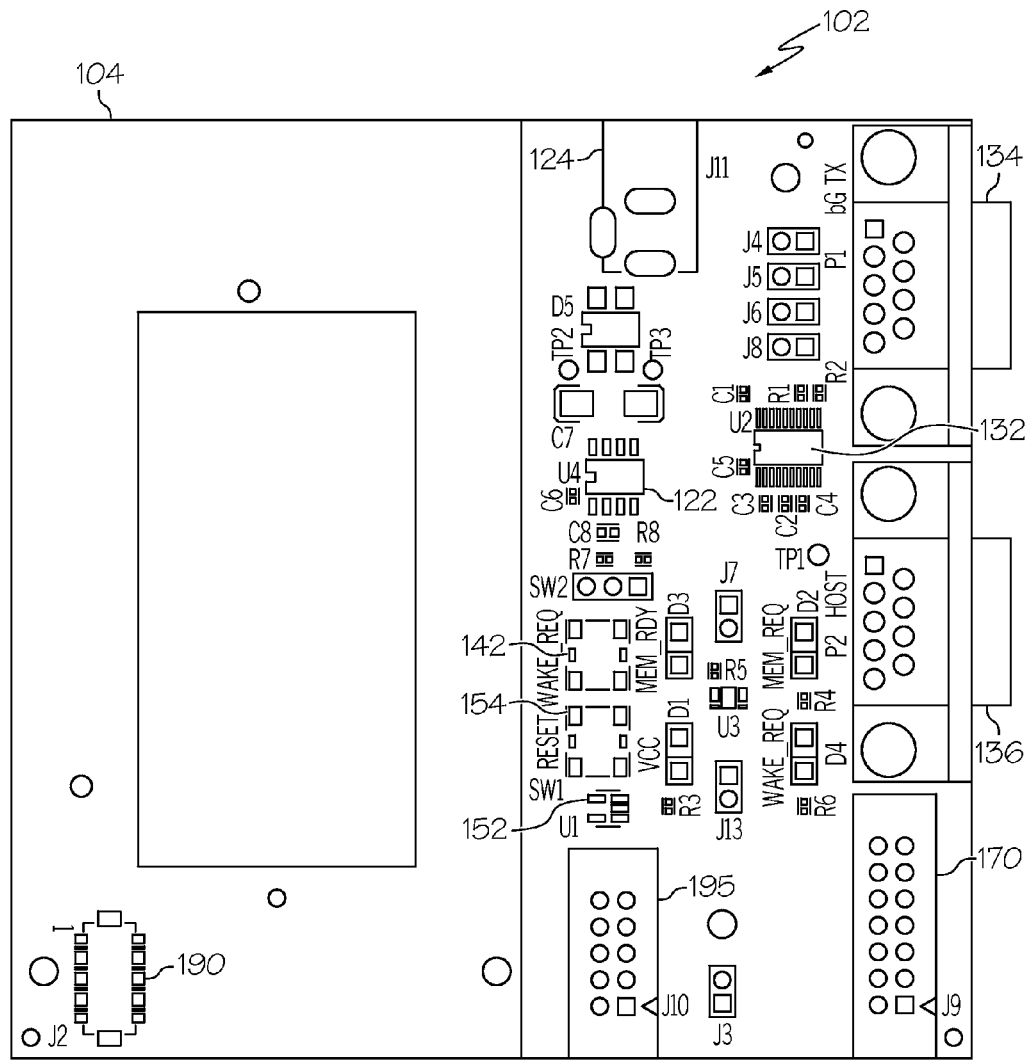
FIG. 11 schematically depicts the component layout of a top surface of a host device emulator according to one or more embodiments shown and described herein.
Figure 12:
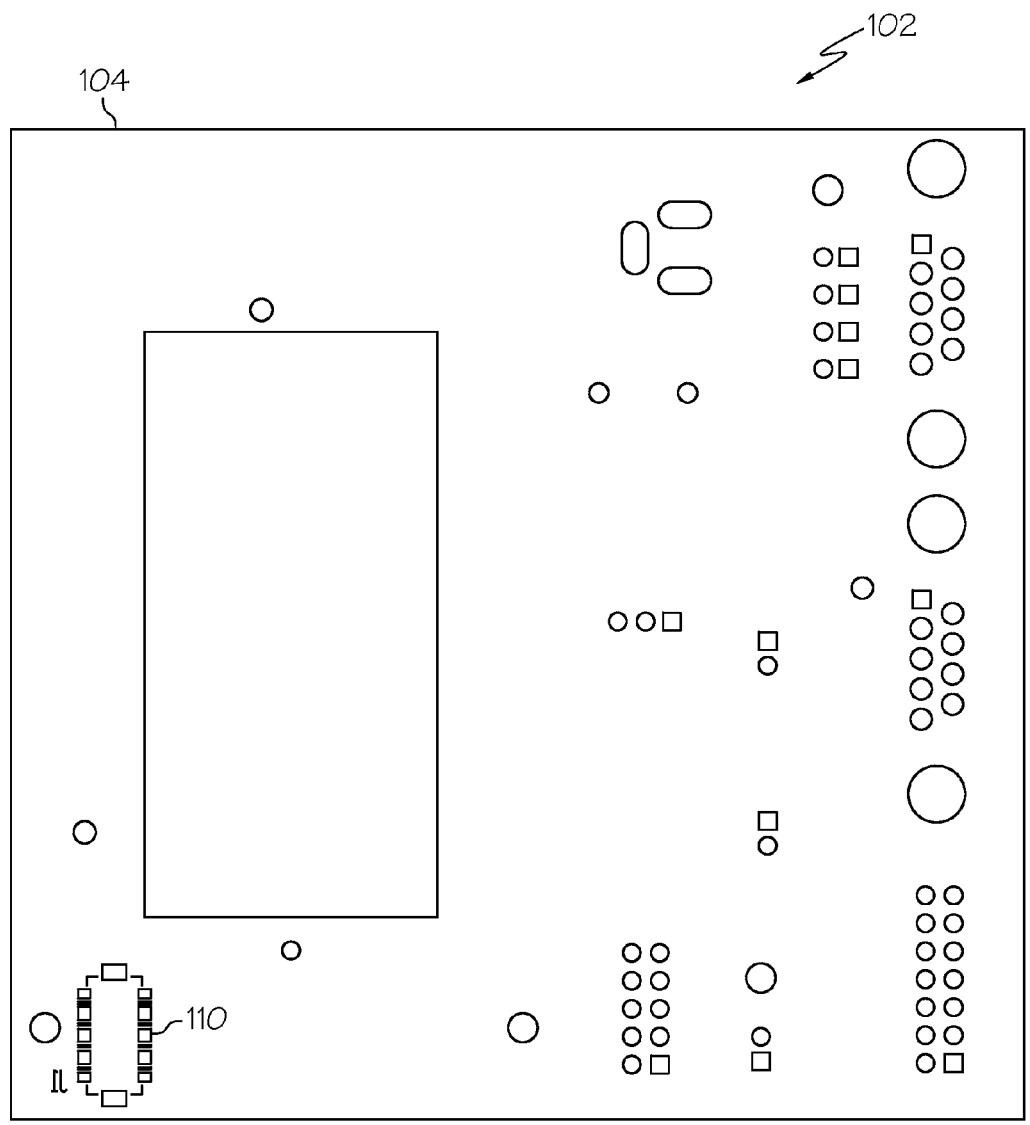
FIG. 12 schematically depicts the component layout of a bottom surface of a host device emulator according to one or more embodiments shown and described herein.
Figure 13:
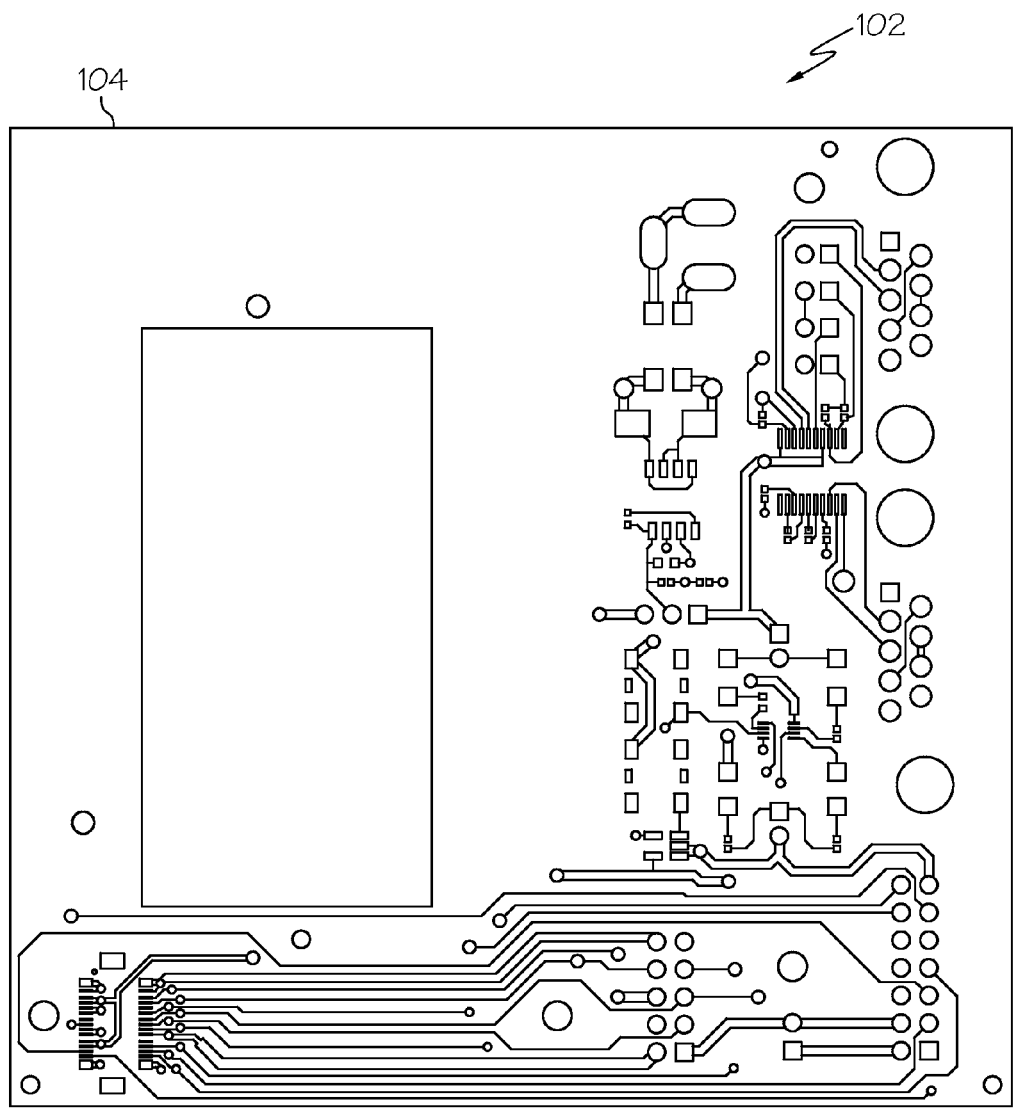
FIG. 13 schematically depicts the conductive traces interconnecting various components on the top surface of a host device emulator according to one or more embodiments shown and described herein.
Figure 14:
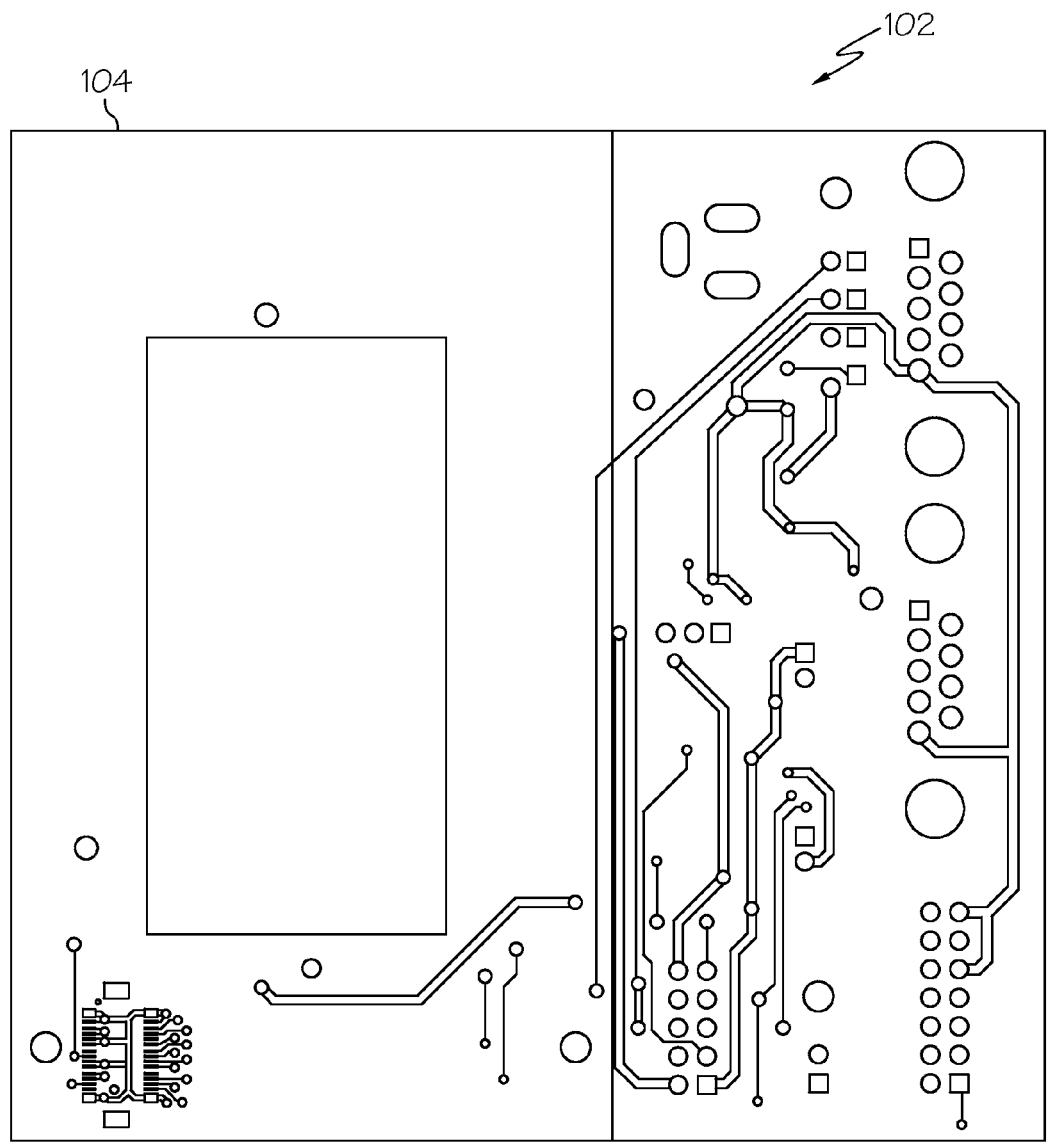
FIG. 14 schematically depicts the conductive traces interconnecting various components on the bottom surface of a host device emulator according to one or more embodiments shown and described herein.

Referring now to FIGS. 11-14, the host device emulator 102 described herein may be constructed by positioning the various components depicted in FIGS. 2-10 on a printed circuit board (PCB) 104 having the appropriate conductive traces to facilitate the desired interconnectivity of the components. For example, FIG. 11 depicts one embodiment of the top surface of a host device emulator 102 showing the relative layout of the various electronic components shown in FIGS. 2-10. As depicted in FIG. 11, the host device port 190 is located on the top surface of the host device emulator 102 along with the various electronic components which comprise the communications port, the power supply, the at least one indicator, the wake request circuit, the programming port, the expansion port and the reset circuit. FIG. 12 shows the component layout of the bottom surface of the host device emulator 102 as viewed from the top surface of the host device emulator 102. As shown in FIG. 12, the measurement engine port 110 is located on the bottom surface of the host device emulator 102 directly opposite the host device port 190. This orientation facilitates directly coupling the host device port 190 with the measurement engine port 110. FIGS. 13 and 14 depict the conductive traces on the top surface and bottom surface of the PCB 104 shown in FIGS. 11 and 12, respectively.

While FIGS. 11-14 depict one exemplary embodiment of a PCB 104 and the respective components utilized to construct the host device emulator 102, it should be understood that other component orientations and/or layouts may be possible to construct a host device emulator 102 having the desired functionality.

The operation of the system 100 for testing a blood glucose measurement engine will now be described with specific reference to FIGS. 1-12. In one embodiment, testing a blood glucose measurement engine with the system 100 depicted in FIG. 1 includes coupling a blood glucose measurement engine to the measurement engine port 110 on the bottom surface of the host device emulator 102 by inserting the printed circuit board of the blood glucose measurement engine into the PCB connector 112 of the measurement engine port 110 such that the blood glucose measurement engine is both mechanically, electrically and communicatively coupled to the host device emulator. The host device emulator 102 is also coupled to the diagnostic computer 180 via the communications port 130 and the DB9 female connector 134.

It should be noted that, in this embodiment, a host device is not coupled to the host device emulator and, as such, the diagnostic computer 180 functions as both a diagnostic tool and a simulated host device that provides diagnostic signals and control signals to the measurement engine via the host device emulator 102 and receives data signals from the blood glucose measurement engine via the host device emulator 102.

Once the blood glucose measurement engine is coupled to the host device emulator 102, power is supplied from the power supply 120 to the blood glucose measurement engine via the measurement engine port 110 causing the power-on indicator (i.e., the second red LED 164) to illuminate. Thereafter, the wake request switch 142 may be activated which, in turn, causes a wake request signal to be sent to the blood glucose measurement engine via the measurement engine port 110. As the wake request signal is sent, the wake request indicator (i.e., the first red LED 163) is illuminated and the blood glucose measurement engine is powered on.

Once the blood glucose measurement engine is powered on, the measurement engine ready indicator (i.e., the green LED 162) is illuminated indicating that the blood glucose measurement engine is ready to receive instructions from the diagnostic computer 180. At this point, the diagnostic computer may be used to run diagnostic programs to test the operability and functionality of the blood glucose measurement engine, query the measurement engine for stored test data for analysis and qualification (i.e., determining if glucose measurements made with the blood glucose measurement engine on a glucose test standard match the standard values) or update and/or modify the programmed instruction sets stored in a memory operatively associated with the blood glucose measurement engine.

For example, in one embodiment, the diagnostic computer performs the functions of a host device and initiates a blood glucose measurement test by sending a control signal to the blood glucose measurement engine via the communications port 130 and the measurement engine port 110. Once the test is initiated, an operator inserts a test strip into the blood glucose measurement engine. The blood glucose measurement engine then tests the strip to verify that the test strip is valid. Once the test strip has been verified, the blood glucose measurement engine then sends a measurement engine request signal to the diagnostic computer via the measurement engine port 110 and the communications port 130 causing the measurement engine request indicator (i.e., the orange LED 161) to illuminate. The measurement engine request signal to the diagnostic computer 180 indicates that the blood glucose measurement engine is ready to perform a blood glucose measurement. The diagnostic computer 180 then sends a control signal to the blood glucose measurement engine via the communications port 130 and the measurement engine port 110 instructing the blood glucose measurement engine to perform a glucose measurement. The measurement engine request indicator is illuminated as the control signal is sent to the blood glucose measurement engine. As these various signals are exchanged between the blood glucose measurement engine and the diagnostic computer 180, the diagnostic computer monitors the signals and, in one embodiment, stores the signals received from the blood glucose measurement engine in memory for subsequent analysis.

Once the blood glucose measurement engine receives the control signal from the diagnostic computer 180, the blood glucose measurement engine performs a glucose measurement on the test strip. During the test the measurement engine ready indicator is dark indicating that the blood glucose measurement engine is "working" and unable to receive additional control signals from the diagnostic computer. However, the diagnostic computer 180 may be used to monitor each step of the measurement process via the host device emulator 102. For example, the diagnostic computer 180 may be used to control the blood glucose measurement engine during the glucose measurement process by stepping the blood glucose measurement engine through each instruction of the glucose measurement process and pausing the blood glucose measurement engine after each instruction of the measurement process is performed. In this manner, the diagnostic computer may be used to ensure that each step of the glucose measurement process is properly performed by the glucose measurement engine.

Once the glucose measurement is performed, the measurement engine ready indicator is illuminated and a measurement engine request signal indicating that the glucose measurement has been performed and that test data is ready is communicated to the diagnostic computer 180 via the measurement engine port 110 and the communications port 130 of the host device emulator 102. The measurement engine request indicator is illuminated as the measurement engine request signal is communicated to the diagnostic computer 180. The blood glucose measurement engine then communicates the value of the test data and an error signal to the diagnostic computer 180 for analysis and qualification. Once the test data and error signal are received from the blood glucose measurement engine, the diagnostic computer 180 provides a control signal to the blood glucose measurement engine signaling the engine to shut down.

Thereafter, the data derived from the glucose measurement test on the standardized glucose solution may be analyzed to qualify the measurement and/or provide calibration of the blood glucose measurement engine. It should also be understood that the performance of the blood glucose measurement engine throughout the glucose measurement may also be assessed to determine if the blood glucose measurement engine functioned properly based on the various signals received from the blood glucose measurement engine and/or monitored with the diagnostic computer 180 during the glucose measurement. Accordingly, it should be understood that the system 100 may be used to test the functionality of the blood glucose measurement engine as well as to qualify and/or calibrate the blood glucose engine relative to a standardized glucose solution.

It should also be understood that the functionality and status of the blood glucose measurement engine may be visually assessed by an operator by monitoring the various indicators during operation of the blood glucose measurement engine. For example, the indicators may be used to determine if the blood glucose measurement engine is ready to send or receive electronic signals at the appropriate times, if the blood glucose measurement engine has stalled during operation, and/or if the blood glucose measurement engine is sending and receiving electronic signals at the appropriate times. Where the blood glucose measurement engine fails to function properly during operation, an operator may manually reset the blood glucose measurement engine using the reset circuit 150. Thereafter, the cause of the malfunction may be diagnosed with the diagnostic computer 180 by evaluating the electronic signals sent to and received from the blood glucose measurement engine during operation.

In another embodiment, a host device is communicatively coupled to the host device emulator by inserting the host device into the PCB connector 192 of the host device port 190 such that the host device is both mechanically, electrically and communicatively coupled to the host device emulator. In this embodiment, the host device emulator 102 is also coupled to the diagnostic computer 180 via the communications port 130 via the DB9 female connector 136 which connection is used to monitor signals to and from the host device. Thereafter, the host device is used to initiate a glucose measurement with the blood glucose measurement engine as the diagnostic computer 180 monitors the control signals and data signals exchanged between the blood glucose measurement engine and the host device. Once the glucose measurement is completed, the test data may be downloaded to the diagnostic computer from the blood glucose measurement engine and analyzed to qualify and/or calibrate the blood glucose measurement engine. Also, the functionality of the blood glucose measurement engine may be assessed based on the signals exchanged between the blood glucose measurement engine and the host device during the glucose measurement.

In either of the aforementioned methods of using the system 100 to test the functionality of a blood glucose measurement engine the diagnostic computer 180 may be used to provide diagnostic signals to the blood glucose measurement engine via the communications port and the measurement engine port to assess the operability of discrete functions and/or process steps performed by the blood glucose measurement engine. Further, the diagnostic computer 180 may be used to calibrate or recalibrate the blood glucose measurement engine based on the test data derived from the glucose measurement performed on the standardized glucose solution.

Further, it should also be understood that the system 100 may also be used to test the functionality of the blood glucose measurement engine under controlled laboratory conditions. For example, the system 100 may be used to endurance test a blood glucose measurement engine to ensure consistency of test data over multiple glucose measurements. Similarly, the system 100 may be used to test a blood glucose measurement engine under varied environmental conditions such as temperature and/or humidity.

While methods of using the system 100 to test the functionality of the blood glucose measurement engine and/or qualify data derived from the blood glucose measurement engine have been described herein, it should be understood that the system 100 and/or the host device emulator 102 may be used for other purposes. For example, in one embodiment, the host device emulator 102 may be used in manufacturing a blood glucose measurement engine to facilitate programming the blood glucose measurement engine. In this embodiment, the host device emulator 102 may be coupled to a newly manufactured blood glucose measurement engine via the measurement engine port 110. The programming port 170 may be communicatively coupled to a computer or a processor which is operable to download computer readable and executable instructions to the blood glucose measurement engine. Accordingly, it should be understood that the host device emulator may be used to program the blood glucose measurement engine.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system for testing a blood glucose measurement engine which performs a glucose measurement process that provides data signals in response to receiving control signals and diagnostic signals, said system comprising:

a host device emulator comprising a measurement engine port communicatively coupled to a communications port and electrically coupled to a power supply; and a diagnostic computer communicatively coupled to the communications port of the host device emulator, the diagnostic computer comprising a processor and a memory having computer readable and executable instructions, and provides the control signals and the diagnostic signals to the blood glucose measurement engine, wherein:

when the blood glucose measurement engine is communicatively coupled to the measurement engine port, the host device emulator simulates a connection to a host device by facilitating communication of the data signals, the control signals and the diagnostic signals between the diagnostic computer and the blood glucose measurement engine, and the processor executes the computer readable and executable instructions to:

transmit the control signals and the diagnostic signals from the diagnostic computer to the blood glucose measurement engine, receive and analyze the data signals transmitted from the blood glucose measurement engine, step the blood glucose measurement engine through the glucose measurement process, monitor a glucose measurement process performed by the blood glucose measurement engine, and pause the blood glucose measurement engine after an instruction of the glucose measurement process has been performed.

2. The system of claim 1 wherein the host device emulator further comprises a host device port communicatively coupled to the measurement engine port, the communications port and the power supply; and the computer readable and executable instructions are executed by the processor to monitor data signals and control signals exchanged between the blood glucose measurement engine communicatively coupled to the measurement engine port and the host device communicatively coupled to the host device port.

3. The system of claim 2 wherein, when a host device is coupled to the host device port, the host device is powered by the power supply.

4. The system of claim 1 wherein the computer readable and executable instructions are executed by the processor to calibrate the blood glucose measurement engine.

5. The system of claim 1 further comprising a wake request indicator, a measurement engine request indicator, and a measurement engine ready indicator, wherein:

the wake request indicator is electrically coupled to the measurement engine port and provides a visual or audible signal when a wake request signal is transmitted to the measurement engine port;

the measurement engine request indicator is electrically coupled to the measurement engine port and provides a visual or audible signal when an electronic signal is transmitted to or from the measurement engine port; and the measurement engine ready indicator is electrically coupled to the measurement engine port and provides a visual or audible signal when the blood glucose measurement engine is communicatively coupled to the measurement engine port and the blood glucose measurement engine is ready to receive a control signal or transmit a data signal.

6. The system of claim 1 wherein the communications port of the host device emulator comprises an RS232 interface.

7. The system of claim 1 wherein the host device emulator comprises a reset circuit communicatively coupled to the measurement engine port.

8. The system of claim 7 wherein the reset circuit comprises a manual reset switch.

9. The system of claim 1 wherein the host device emulator comprises a wake request circuit communicatively coupled to the measurement engine port.

10. The system of claim 9 wherein the wake request circuit comprises a manual wake request switch.

11. The system of claim 1 wherein the host device emulator comprises a programming port communicatively coupled to the measurement engine port.

12. The system of claim 11 wherein the programming port comprises a processor communicatively coupled to a memory in which computer readable and executable instructions are stored and the processor is operable to execute the instructions to upload an instruction set to the blood glucose measurement engine communicatively coupled to the measurement engine port.

13. The system of claim 1 wherein the host device emulator further comprises an expansion port communicatively coupled to the measurement engine port.

14. The system of claim 1 wherein, when the blood glucose measurement engine is coupled to the measurement engine port, the blood glucose measurement engine is powered by the power supply.

15. A host device emulator for facilitating communications between a blood glucose measurement engine and a diagnostic computer in which the communications comprise data signals from the blood glucose measurement and control signals and diagnostic signals from the diagnostic computer, and in which the blood glucose measurement engine performs a glucose measurement process, the host device emulator comprising:
 a power supply;
 a communication port electrically coupled to the power supply and communicatively connectable to the diagnostic computer;
 a measurement engine port communicatively coupled to the communications port and electrically coupled to at least one indicator and the power supply, wherein the measurement engine port is communicatively connectable to the blood glucose measurement engine;
 a host device port electrically coupled to the power supply and communicatively coupled to the measurement engine port and the communications port, wherein the host device port is communicatively connectable to the host device and, wherein the measurement engine port, the host device port and the communications port are operable to:
  facilitate communication of the data signals, the control signals and the diagnostic signals between the diagnostic computer and the blood glucose measurement engine;
  facilitate communication of the data signals and the control signals between the host device and the blood glucose measurement engine; and
  facilitate use of the diagnostic computer to monitor the data signals and the control signals between the host device and the blood glucose measurement engine, to step the blood glucose measurement engine through the glucose measurement process, and to pause the blood glucose measurement engine after an instruction of the glucose measurement process has been performed.

16. The host device emulator of claim 15 wherein the at least one indicator comprises a wake request indicator, a measurement engine request indicator, and a measurement engine ready indicator, wherein:
 the wake request indicator is electrically coupled to the measurement engine port and provides a visual or audible signal when a wake request signal is transmitted to the measurement engine port;
 the measurement engine request indicator is electrically coupled to the measurement engine port and provides a visual or audible signal when an electronic signal is transmitted to or from the measurement engine port; and
 the measurement engine ready indicator is electrically coupled to the measurement engine port and provides a visual or audible signal when the blood glucose measurement engine is communicatively coupled to the measurement engine port and the blood glucose measurement engine is ready to receive a control signal or transmit a data signal.

17. The host device emulator of claim 15 wherein the communications port comprises an RS232 interface.

18. The host device emulator of claim 15 further comprising:
 a reset circuit communicatively coupled to the measurement engine port, wherein the reset circuit comprises a reset switch for manually initiating a reset signal to the measurement engine port; and
 a wake request circuit communicatively coupled to the measurement engine port, wherein the reset circuit comprises a wake request switch for manually initiating a wake request signal to the measurement engine port.

19. The host device emulator of claim 15 further comprising a programming port communicatively coupled to the measurement engine port.

* * * * *